United States Patent
Domke et al.

(10) Patent No.: US 8,510,062 B2
(45) Date of Patent: Aug. 13, 2013

(54) METHOD FOR ASSESSING A STATE OF A DOCUMENT OF VALUE WITH REGARD TO LIMPNESS USING ULTRASOUND, AND MEANS FOR CARRYING OUT THE METHOD

(75) Inventors: Jan Domke, München (DE); Klaus Thierauf, München (DE); Stefan Kokrhoun, Gröbenzell (DE); Franz Müller, München (DE)

(73) Assignee: Giesecke & Devrient GmbH, Munich (DE)

( * ) Notice: Subject to any disclaimer, the term of this patent is extended or adjusted under 35 U.S.C. 154(b) by 706 days.

(21) Appl. No.: 12/374,302

(22) PCT Filed: Jul. 12, 2007

(86) PCT No.: PCT/EP2007/006212
§ 371 (c)(1),
(2), (4) Date: Jan. 17, 2009

(87) PCT Pub. No.: WO2008/009384
PCT Pub. Date: Jan. 24, 2008

(65) Prior Publication Data
US 2009/0312957 A1    Dec. 17, 2009

(30) Foreign Application Priority Data
Jul. 17, 2006    (DE) .................. 10 2006 033 001

(51) Int. Cl.
*G01B 5/28*    (2006.01)
*G01N 29/27*    (2006.01)
*G01N 29/04*    (2006.01)

(52) U.S. Cl.
USPC ............... 702/39; 702/34; 702/35; 702/189; 73/596; 73/602; 73/628

(58) Field of Classification Search
USPC ............... 702/34, 35, 39, 189; 73/596, 602, 73/628
See application file for complete search history.

(56) References Cited

U.S. PATENT DOCUMENTS

| 6,407,964 B1 | 6/2002 | Hornung et al. |
| 6,595,060 B2 | 7/2003 | Wunderer et al. |

(Continued)

FOREIGN PATENT DOCUMENTS

| DE | 198 44 447 A1 | 9/1998 |
| DE | 101 37 389 A1 | 7/2001 |

(Continued)

OTHER PUBLICATIONS

German Search Report issued in German application No. 10 2006 0033 001.3, mailed Jan. 8, 2007, 4 pages.

(Continued)

*Primary Examiner* — Andrew Schechter
*Assistant Examiner* — L. Anderson
(74) *Attorney, Agent, or Firm* — Bacon & Thomas, PLLC

(57) ABSTRACT

In a method for assessing a condition of at least one value document with regard to limpness, there is determined from transmission values representing the ultrasound transmission at different places on the value document a condition value which depends on a variation of the transmission values and characterizes the condition of the value document with regard to limpness. A condition of the value document is determined for the condition value using a preset criterion.

48 Claims, 4 Drawing Sheets

(56) References Cited

U.S. PATENT DOCUMENTS

| | | |
|---|---|---|
| 6,673,721 B1 | 1/2004 | Kim et al. |
| 6,745,628 B2 | 6/2004 | Wunderer |
| 7,469,589 B2 | 12/2008 | Pradel |
| 7,571,796 B2 * | 8/2009 | Stenzel et al. ............ 194/206 |
| 2002/0014120 A1 | 2/2002 | Wunderer et al. |
| 2003/0025512 A1 | 2/2003 | Wunderer |
| 2003/0183012 A1 | 10/2003 | Wunderer et al. |
| 2007/0006654 A1 | 1/2007 | Pradel |
| 2007/0187209 A1 | 8/2007 | Stenzel et al. |

FOREIGN PATENT DOCUMENTS

| | | |
|---|---|---|
| DE | 100 29 442 A1 | 1/2002 |
| DE | 103 18 756 A1 | 11/2004 |
| DE | 103 18 104 A1 | 4/2009 |
| RU | 2002120198 A | 3/2004 |
| WO | WO 02/10716 A | 2/2002 |
| WO | WO 2004/095380 A | 11/2004 |
| WO | 2005013207 A1 | 2/2005 |

OTHER PUBLICATIONS

English Abstract of DE 10137389 (A1), published Nov. 11, 2004.
Knjazev and Tscherkasskij, "Measuring practice, fundamentals of the processing of experimental data", 1996, Novosibirsk State University.
Machine Translation of Knjazev and Tscherkasskij, "Measuring practice, fundamentals of the processing of experimental data".
Machine Translation of Abstract and Claims for RU2002120198.

* cited by examiner

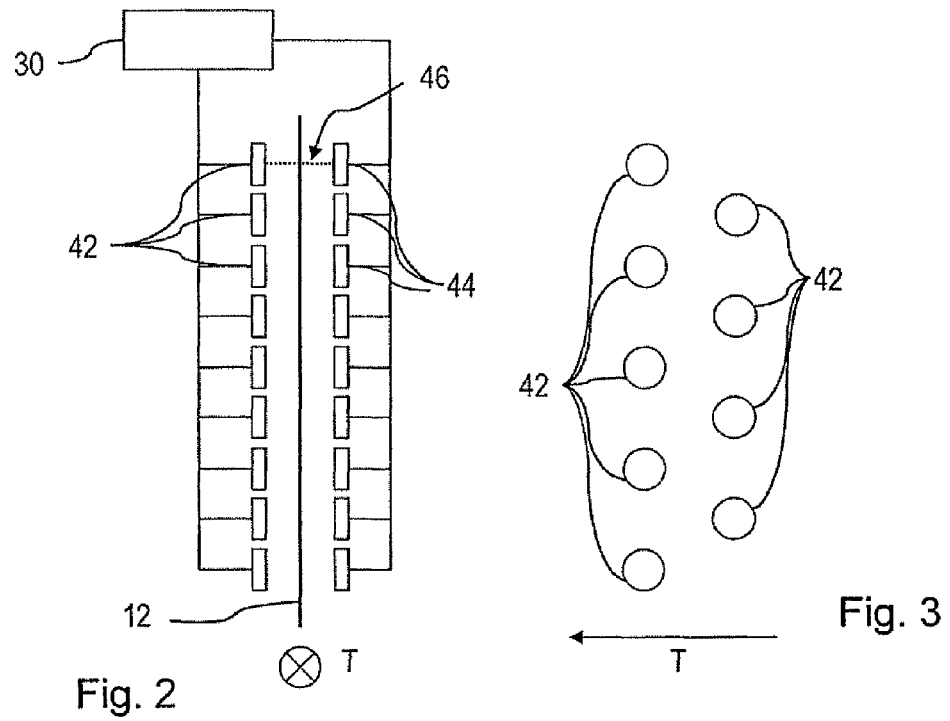
Fig. 2
Fig. 3
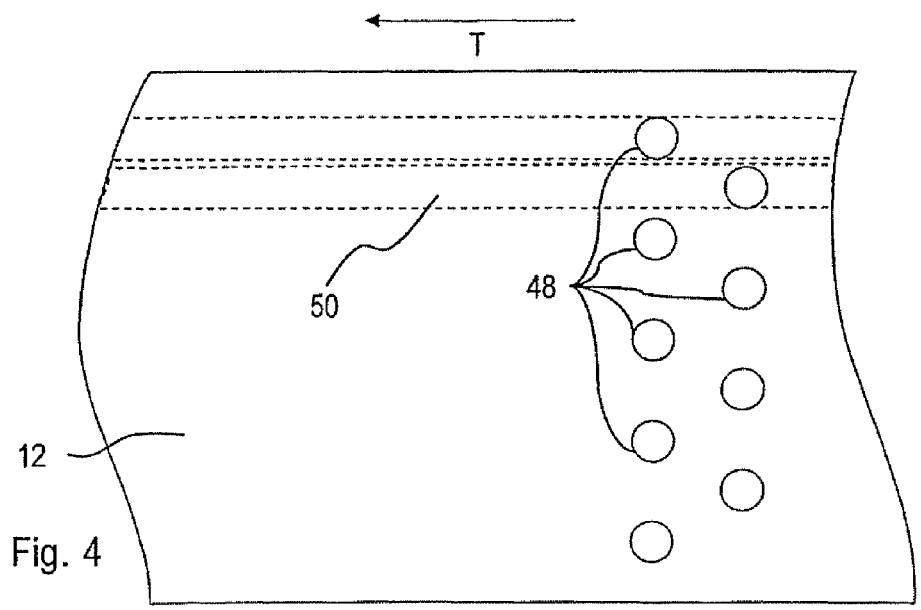
Fig. 4

METHOD FOR ASSESSING A STATE OF A DOCUMENT OF VALUE WITH REGARD TO LIMPNESS USING ULTRASOUND, AND MEANS FOR CARRYING OUT THE METHOD

FIELD OF THE INVENTION

The present invention relates to a method for assessing a condition of at least one value document with regard to limpness, and to means for carrying out said method.

BACKGROUND

Value documents will be understood here and in the following to mean sheet-shaped objects that represent for example a monetary value or an authorization and are therefore not to be producible at will by unauthorized persons. They therefore have features that are not easy to produce, in particular to copy, whose presence is an indication of authenticity, i.e. production by an authorized body. Important examples of such value documents, which can have in particular one or more layers of film and/or paper, are coupons, vouchers, checks and in particular bank notes.

In case of repeated and in particular not very careful use, such value documents can have properties or a condition that are changed compared to new, unused value documents. In particular, value documents such as bank notes can become limp. Limpness is understood here to mean a condition in which the bank note has considerably less stiffness or easier deformability and/or less elasticity than in the mint condition.

This change of condition of value documents can strongly reduce or even rule out their processibility by machine. Thus, bank notes whose limpness exceeds a certain measure are characterized as no longer fit for use, removed from circulation and replaced by new bank notes. The condition can therefore be determined as "fit for use" or as "to be destroyed".

To permit a large number of value documents to be evaluated with regard to limpness, it is necessary to have a method for checking the condition of value documents with regard to limpness that is as reliable, gentle and simple as possible and can be carried out by machine.

At the time of filing, the condition with regard to limpness is frequently checked using a mechanical method wherein for example a bank note is deformed, in particular slightly bent, and the sound development occurring upon deformation is detected and evaluated. This method provides reliable results, but the bank notes are worn further by the deformation.

SUMMARY

The invention is therefore based on the object of providing a method for determining the condition of a value document with regard to limpness that avoids high wear of the value documents, and means for carrying out said method.

This object is achieved by a method for assessing a condition of at least one value document with regard to limpness wherein there is determined from transmission values representing the ultrasound transmission at different places on the value document a condition value which depends on a variation of the transmission values and characterizes the condition of the value document with regard to limpness, and a condition of the value document is determined for the condition value using a preset criterion.

The object is further achieved by an evaluation device for assessing a condition of at least one value document with regard to limpness which is so configured that it determines from transmission values representing the ultrasound transmission at different places on the value document a condition value which depends on a variation of the transmission values and characterizes the condition of the value document with regard to limpness, and determines a condition of the value document for the condition value using a preset criterion.

The evaluation device can in principle be configured independently of a device for detecting the transmission values. It then only needs to have an interface or a reading apparatus for data carriers by means of which transmission values or transmission data can be read in. However, the devices are preferably integrated. The object is therefore also achieved by an apparatus for assessing a condition of at least one value document with regard to limpness having at least one ultrasound transmitter and at least one ultrasound receiver located opposite each other to form an ultrasound path for a detection of the transmission at a place on the value document, an inventive evaluation device, and an interface between the ultrasound receiver and the evaluation device, by means of which transmission signals from the ultrasound receiver representing transmission values are supplied to the evaluation device for assessing the condition of the value document. Where necessary, the evaluation device can be configured in particular for carrying out a conversion of transmission signals to transmission values.

For assessing the limpness of the value document the invention thus does not use a single transmission value or average of transmission values, but rather a variation of the transmission values, i.e. a change or fluctuation of the transmission values from place to place on the value document. It is preferable to use at least five, preferably more, transmission values which in each case correspond or are assigned to different places on the value document. Surprisingly, a thus formed condition value can be used as a measure of the limpness of a value document and offer at least the same reliability as the above-mentioned non-contactless method, or even higher reliability.

The condition is assessed using the preset criterion which includes the condition value. In dependence on whether the criterion is met, the condition of the value document can then be specified for example as "fit for use" or "no longer fit for use", that is, "to be destroyed". The criterion can also depend on further parameters which can likewise have an influence on the fitness for use, for example defects of the value document. According to the result of the check of the criterion, a signal representing the result of the check can be formed or a corresponding datum stored. It is also possible to directly drive a following device, for example a transport device or sorting device for transporting or sorting the value documents according to the determined condition, so that the value document is handled further according to its condition.

The method works contactlessly, so that the value documents can be assessed gently. Further, the noise burden in the audible range is strongly reduced compared to the method according to the prior art.

Furthermore, the method has surprisingly turned out to be more reliable than the above-described method according to the prior art. In particular, the results are better reproducible.

The evaluation device can in principle be configured at will and have for example a predetermined analog or in particular digital circuit for processing the transmission values which is configured for carrying out the inventive method. However, the evaluation device preferably comprises a processor, a memory storing a computer program for execution by the processor, upon whose execution the processor carries out the inventive method, and an interface for detecting signals or data from which the transmission values and/or the variation of the transmission values can be determined or which represent the transmission values.

The subject of the invention is therefore also a computer program for execution by means of a data processing device having a processor which contains program code upon whose execution the processor carries out the inventive method and in particular determines from transmission values representing the ultrasound transmission at different places on the value document a condition value which depends on a variation of the transmission values and characterizes the condition of the value document, and determines a condition of the value document for the condition value using a preset criterion. Said computer program can in particular be stored in the above-mentioned memory.

This embodiment offers the advantage that, firstly, standard components can be used for the evaluation device and, secondly, the processor can also perform other functions.

A processor is understood in the context of the present invention to mean not only an individual processor with one or more cores, but also a system of coupled processors. It is further possible to use as a processor for example a multipurpose processor, for example for customary personal computers, or a digital signal processor. Furthermore, the processor can also comprise an FPGA.

Further preferred embodiments and developments are described in the claims, the description and the figures.

The method and the computer program preferably use no reflectance values, i.e. intensity values of reflected ultrasound, for determining the condition value.

The ultrasound transmission values can in principle be detected in any desired way. For example, the places can be irradiated continuously with focused ultrasound in parallel or in succession. However, it is preferred that, in the method, ultrasound pulses are emitted onto at least two different places on the value document and ultrasound pulses emanating from the places as a result of the ultrasound pulses are detected so as to form the transmission values. This permits the method to be carried out particularly fast. The pulse lengths are preferably selected to be short, but at least long enough to permit a frequency to be assigned in good approximation to the ultrasound pulse.

The emission of the ultrasound pulses can be effected independently of the evaluation of the transmission values, for example triggered by a separate circuit. However, in the apparatus, the evaluation device is preferably connected to the ultrasound transmitter for the drive thereof and configured for driving the ultrasound transmitter to emit ultrasound pulses.

Surprisingly, it has been ascertained that particularly good results can be achieved with the method when the ultrasound has an ultrasound frequency greater than 300 kHz. In the apparatus, the at least one ultrasound transmitter is for this purpose preferably configured for emitting ultrasound at an ultrasound frequency greater than 300 kHz.

Further, it has surprisingly been found that particularly good results are obtained with the method when spots on the value document irradiated in each case by the ultrasound have a diameter smaller than 3.5 mm. For this purpose, the apparatus and in particular the ultrasonic sensor thereof are configured for emitting ultrasound that irradiates a spot with a diameter smaller than 3.5 mm when impinging on a value document disposed at a preset distance from the ultrasonic sensor. In this case the variations due to limpness of the value document are particularly pronounced. The ultrasound can be emitted in particular in the form of beams. The diameter can be determined for example by examining a sample with areas of reduced transmission that are as sharply delimited as possible, for example a bank note with an adhesive strip. For this purpose, the spot is moved relative to the sample across the portion in which the transmission changes as abruptly as possible. The relative motion is selected so that ultrasound transmission values are detected along a direction orthogonal to the boundary between the areas of different transmission at spatial intervals that are substantially smaller than the expected diameter of the spot. The corresponding curve of the transmission values as a function of place yields a continuous drop from a plateau with high transmission values to a plateau of lower transmission values which results when the area of lower transmission is selected to be considerably wider than the expected spot diameter. The width of the area where the transmission drops then corresponds to the spot diameter and can be used as the value for spot diameter. The width can be determined by adapting to the curve of the transmission values a continuous function with three adjacent areas in which the latter shows a linear curve. The width of the middle area can be used as the spot diameter.

The detection of the transmission values can be effected in principle in any desired way. In particular, the possibilities stated hereinafter can be used alternatively or in combination with each other. According to a first possibility, in the method, the value document is moved for detecting the transmission values. The apparatus can for this purpose preferably have a transport device for transporting the value document through the ultrasound path, and the evaluation device can be configured for successively detecting transmission values corresponding to at least five different places on the value document and evaluating them.

The places need in principle not be specified by coordinates or other explicit indications of place, depending on the way the variation is determined. However, it is possible to determine the position thereof in the stated possibility by the time interval between the detection times and by the transport speed or—in the case of detection at constant time intervals—only by the order at least relative to each other.

According to a second possibility, in the method, at least two ultrasound paths can be used for detecting the transmission values. The apparatus can for this purpose preferably comprise at least one further ultrasound path, and the evaluation device can be configured for evaluating transmission signals detected along the further ultrasound path. For providing the further ultrasound path the apparatus can have in particular a further ultrasound transmitter and a further ultrasound receiver.

Upon use of a plurality of ultrasound paths, the transmission values can be detected in succession when there is a danger of crosstalk occurring between the ultrasound paths. However, if the transmission values are to be detected as fast as possible, the transmission values, in the method, are determined simultaneously preferably for at least two different places. The evaluation device is for this purpose preferably so configured that it drives ultrasound transmitters for the ultrasound paths such that they emit ultrasound pulses simultaneously. Simultaneous emission is understood here to mean that two ultrasound pulses are emitted at the most at a time interval smaller than the duration of one of the ultrasound pulses. Further, ultrasound pulses need not be emitted simultaneously on all ultrasound paths used, when more than two ultrasound paths are used.

A further possibility for detecting the transmission values is to change the alignment of the ultrasound path for detecting the transmission values. For this purpose, the ultrasound transmitter and/or the ultrasound receiver can be movable relative to the area under examination, and the evaluation device determines the transmission values in dependence on the position of the ultrasound transmitter or ultrasound receiver.

The places for which the transmission values are detected can in principle be selected at will; in particular, the condition value needs to be determined only for a portion of the value document. However, the places preferably cover as large an area of the value document as possible.

Thus, in the method, the places can be distributed randomly. This embodiment has the advantage that systematic errors caused by the arrangement of the places can be largely avoided.

It is more favorable for carrying out the method, however, that the places are distributed regularly. In particular upon detection of the transmission values with motion of the value document, such a distribution of places already results upon a detection at constant time intervals.

In particular, in the method, the places can be disposed within a linear strip, preferably parallel to a transport direction of the value documents. This arrangement is suitable in particular when one or more ultrasound transmitters and receivers disposed transversely to the transport direction are used for detecting the transmission values.

In this case it is particularly preferable that, in the method, the places are disposed within at least two strips. The apparatus can for this purpose preferably have at least one further ultrasound receiver for detecting transmission values which is spaced from the at least one ultrasound receiver in a preset direction. The preset direction is preferably aligned to be orthogonal or inclined relative to a transport direction of the value document, if the latter is moved upon detection of the transmission values. This permits a larger surface area of the value document to be assessed, so that the limpness can be determined with greater reliability.

It is in principle only necessary, in the method, to use a set of transmission values for determining the one condition value. However, it is also possible, in the method, that there is determined from further transmission values for different further places on the value document a further condition value which depends on a variation of the further transmission values for the further places, and that the preset criterion additionally includes the further condition value. The evaluation device is then preferably configured for determining from further transmission values for different further places on the value document a further condition value which depends on a variation of the further transmission values for the further places. The preset criterion then additionally includes the further condition value. The computer program can preferably contain program code upon whose execution the processor determines from further transmission values for different further places on the value document a further condition value which depends on a variation of the further transmission values for the further places, which contains program code, so that the preset criterion additionally includes the further condition value. The determination of the further condition value can be effected in particular in the same way as the determination of the condition value. This embodiment has several advantages. Thus, the at least two resulting condition values can be used for checking the reliability of the determination of the condition values. This is the case in particular when the places for the transmission values and the further places for the further transmission values are not located in respective contiguous surface areas on the value document.

However, it is particularly preferable, in the method, for the places for the transmission values and the further places for the further transmission values to be located in each case in separate, contiguous areas. This permits a determination of a condition value with regard to limpness for the individual areas. The determined condition values or further condition values will hereinafter then also be referred to as area condition values. In particular, the areas can be given by the above-mentioned strips. The apparatus with the evaluation device configured as mentioned above can then preferably be further so configured that the transmission values or further transmission values are determined from transmission signals for the places determined by means of the ultrasound path or further ultrasound path.

Depending on the requirement for the determination of condition, the areas can overlap or have no common place.

Further, the transmission values and further transmission values do not need to be detected separately from each other. Rather, a set of transmission values can be divided into at least two disjoint sets, a first set having the transmission values for determining the condition value and the second or further set having the further transmission values for the further places for determining the further condition value.

The consideration of the variation can be effected in different ways. A particularly pronounced relation between variation and limpness results when this variation is not due to systematic changes in transmission, as are caused for example by watermarks in bank notes, but has a static or random character. To permit systematic changes to be considered to the greatest possible extent, there are several possibilities, whereby at least the three possibilities described hereinafter can be used alternatively or also in combination.

In the method according to a first possibility, it is possible not to use transmission values for places in a preset area of the value document, or to use them with lower weighting than ones for places outside the area, upon determination of the condition value. The evaluation device is for this purpose preferably further so configured that transmission values for places in a preset area are not used, or used with lower weighting than ones for places outside the area, upon determination of the condition value. The computer program can for this purpose preferably contain program code upon whose execution the processor does not use transmission values for places in a preset area, or uses them with lower weighting than ones for places outside the area, upon determination of the condition value. This has the advantage that for example a watermark area or an area with a security thread can be completely disregarded or be considered only with low weighting for determining limpness. The corresponding transmission values need for this purpose either not be detected or can, after detection, simply be left out of consideration in the determination.

Further, in the method, it is possible for transmission values for places in a preset area to be weighted higher than transmission values for other places upon determination of the condition value. For this purpose, the evaluation device is preferably further so configured that transmission values for places in a preset area are weighted higher than transmission values for other places upon determination of the condition value. For this purpose, the computer program can in particular contain program code upon whose execution the processor weights transmission values for places in a preset area higher than transmission values for other places upon determination of the condition value. This embodiment has the same advantages as the above-described embodiment.

In the third possibility, in the method, the transmission values are corrected with respect to a transmission profile preset for the value document, before or upon determination of the condition value. The evaluation device is for this purpose preferably further so configured that the transmission values are corrected with respect to a transmission profile preset for the value document, before or upon determination of the condition value. Accordingly, the computer program can contain program code upon whose execution the processor corrects the transmission values with respect to a transmission profile preset for the value document, before or upon determination of the condition value. This embodiment has the advantage that for assessing the condition of the value document it is also possible to consider areas having a systematic change in the ultrasound transmission, for example an area with a watermark showing a picture or in particular also a bar watermark or bar code watermark. For considering the systematic change, it is in particular possible to subtract the known systematically present or expected transmission profile from the determined transmission values.

To permit corresponding areas or transmission profiles to be correctly selected in the three stated possibilities, it is possible, in the method, to preferably previously determine the type of value document, for example the denomination in the case of bank notes, and to use parameters for selecting the areas or transmission profile from a table stored in the evaluation device containing parameters assigned to possible types of value documents and representing the areas or transmission profile.

For considering the variation optionally corrected with respect to a systematic transmission profile, it is in principle possible to use different methods that quantify the strength of a fluctuation of a variable under examination. It has turned out, however, that some possibilities produce particularly reliable results.

According to a first possibility, it is possible to use deviations of the transmission values from a preset value, preferably an average of the transmission values, for considering the variation. The evaluation device is then preferably configured for using deviations of the transmission values from a preset value, preferably an average of the transmission values, for considering the variation. The computer program can in particular contain program code upon whose execution the processor uses deviations of the transmission values from a preset value, preferably an average of the transmission values, for considering the variation. A deviation can be understood to be for example a ratio of the values. However, the deviation is preferably the difference of the values or an absolute difference of the values. For forming the condition value it is then possible to use any even functions of the differences or any, in particular also odd, functions of the absolute values. In particular, the condition value can depend on a sum of values of an even function of the differences or an odd function of the absolute values. For example, the condition value can be proportional to the variance or the standard deviation of the transmission values. This has the advantage that no information whatsoever about the position of the places for which the transmission values were detected relative to each other or relative to the value document needs to be known.

In another embodiment of the method, deviations between transmission values for different places are used for considering the variation. The evaluation device can then preferably be configured for using deviations between transmission values for different places for considering the variation. For this purpose, the computer program can further have program code upon whose execution the processor uses deviations between transmission values for different places for considering the variation. This embodiment yields particularly good results since the limpness of a value document is influenced by, among other things, local differences in the properties of the value document. Furthermore, the determination can be effected fast.

In particular, it is then preferred that, in the method, the deviations between transmission values for different places used are only deviations between transmission values for places whose distance is no greater than a preset maximum distance. The evaluation device can then preferably be configured for using as deviations between transmission values for different places only deviations between transmission values for places whose distance is no greater than a preset maximum distance. Further, the computer program can preferably contain program code upon whose execution the processor uses as deviations between transmission values for different places only deviations between transmission values for places whose distance is no greater than a preset maximum distance. This embodiment permits particularly fast determination of the condition value. The maximum distance can be preset as the real distance or by the neighborhood to other places. In particular, in a particularly preferred embodiment, only deviations between nearest neighboring places need to be considered.

Alternatively it is possible, in particular upon use of places along a straight line or in a linear strip, to use, in the method, a spectrum of the transmission values for considering the variation. The evaluation device is then preferably configured for using a spectrum of the transmission values for considering the variation. Accordingly, the computer program can hold program code upon whose execution the processor uses a spectrum of the transmission values for considering the variation. The spectrum used can be for example a wavelet spectrum. A particularly fast determination can result upon use of a Fourier spectrum, in particular when fast Fourier transform (FET) methods are used.

A further possibility consists in determining and using, in the method, a distribution function of the transmission values for considering the variation. The evaluation device can then preferably be configured for determining and using a distribution function of the transmission values for considering the variation. In particular, the computer program can then contain program code upon whose execution the processor determines and uses a distribution function of the transmission values for considering the variation. The distribution function can be used for example in such a way that its half width is determined. Upon this evaluation, further information about the transmission values can also be easily obtained.

The transmission values can fluctuate beyond the variation caused by limpness not only due to a systematic or preset variation, for example through the watermark, but also through other properties of the value document which can occur randomly. One example of this is the occurrence of small holes and/or tears in the value document. Holes or tears can lead to exceptionally high transmission values which can impair the determination of limpness.

It is therefore preferred that transmission values deemed atypical according to a preset outlier criterion are not considered, or considered less strongly than other transmission values, upon determination of the condition value. The evaluation device is then preferably further configured for not considering transmission values deemed atypical according to a preset outlier criterion, or considering them less strongly then other transmission values, upon determination of the condition value. In particular, the computer program can preferably contain program code upon whose execution the processor does not consider transmission values deemed atypical according to a preset outlier criterion, or considers them less strongly than other transmission values, upon determination of the condition value.

It can preferably be checked as the outlier criterion whether one of the transmission values is within a preset range. The evaluation device can for this purpose preferably be so configured that it is checked as the outlier criterion whether one of the transmission values is within a preset range. Accordingly, the computer program can preferably contain program code upon whose execution the processor checks as the outlier criterion whether one of the transmission values is within a preset range. The preset range can in particular be determined empirically by experiment with value documents of different limpness. This embodiment in particular makes use of the fact that holes and tears lead to variations of the transmission values that substantially differ in their size from variations caused by limpness or corresponding properties in the fine-scale properties of the value document. In particular upon the occurrence of holes and tears it plays a considerable part that the size of a spot acoustically irradiated on the value document at a place is not too great, since otherwise a kind of averaging effect over the limpness-induced fluctuations might occur and the transmission values only reflect holes, tears or other macroscopic structural inhomogeneities such as sharp creases.

The criterion used for the condition value can be in particular a criterion for the size of the condition value, in particular a threshold criterion. The threshold value can be given in dependence on a maximum permissible limpness, which can be preset for example in the case of bank notes by the fitness for use or machine processibility of the bank notes. The criterion for the condition of the value document can include not only the condition value for limpness but also at least one other value or property of the value document, for example the presence of adhesive strips or strong soiling.

The result of the check can then be stored, output or used for driving a device of a value-document processing device, for which purpose the evaluation device can be configured accordingly and in particular the computer program can also contain corresponding program code for execution by the processor.

A further subject of the invention is a data carrier on which an inventive computer program is stored. Data carriers that can be used are in particular optical data carriers, such as CDs or DVDs, magneto-optical data carriers, magnetic data carriers, such as hard disks and semiconductor memories, for example flash memories, whose content can be accessed by a corresponding device of a computer.

BRIEF DESCRIPTION OF THE DRAWINGS

The invention will hereinafter be explained more closely by way of example with reference to the drawings. Therein is shown:

FIG. 2 a schematic representation of an ultrasonic sensor of the bank-note processing apparatus in FIG. 1 with a control and evaluation device in a view along a transport direction of bank notes, FIG. 3 a schematic representation of ultrasound transmitters of the ultrasonic sensor in FIG. 2 in a plane parallel to the plane of a bank note under examination, FIG. 4 a schematic partial representation of a bank note with spots or scan areas irradiated by the ultrasound transmitters of the ultrasonic sensor in FIG. 2, FIG. 5 a schematic representation of a bank note with places or scan areas for which transmission values were determined by means of the ultrasonic sensor in FIG. 3, FIG. 6 a simplified flow chart for a method for determining a condition of a bank note by means of the ultrasonic sensor and the control and evaluation device in FIG. 2 according to a preferred embodiment of the invention, and FIG. 7 a simplified flow chart for a method for determining a condition of a bank note by means of the ultrasonic sensor and the control and evaluation device in FIG. 2 according to a further preferred embodiment of the invention.

DETAILED DESCRIPTION OF VARIOUS EMBODIMENTS

Figure 1:
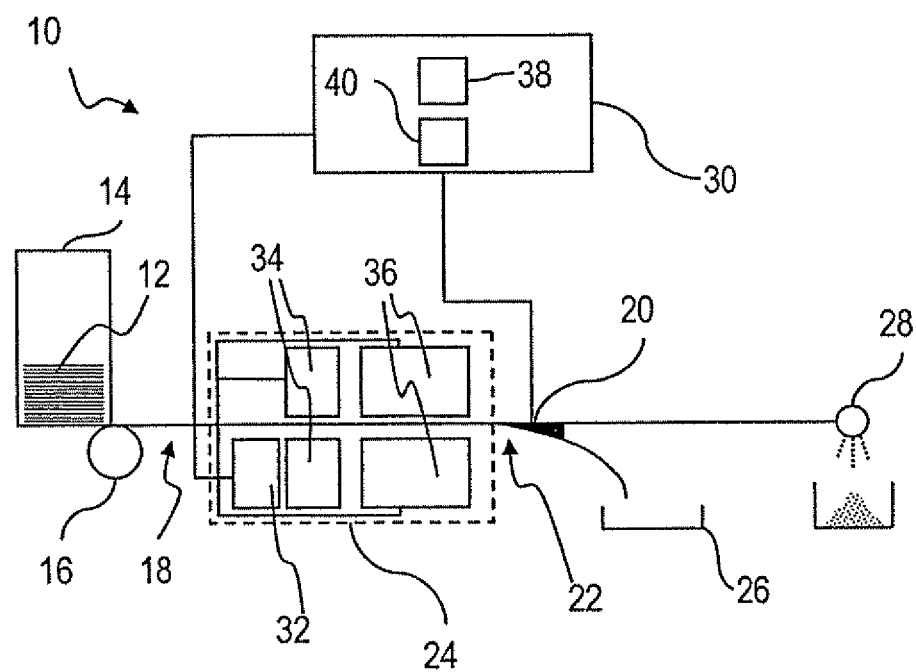
FIG. 1 a schematic representation of a bank-note processing apparatus.

A bank-note processing apparatus 10 in FIG. 1 which comprises an apparatus for determining a condition of value documents in the form of bank notes 12 has an input pocket 14 for the input of bank notes 12 to be processed, a singler 16 which can access bank notes 12 in the input pocket 14, a transport device 18 with a gate 20, and along a transport path 22 given by the transport device 18 a sensor assembly 24 disposed before the gate 20, and after the gate 20 an output pocket 26 and a shredder 28 for destroying bank notes. A control and evaluation device 30 is connected at least to the sensor assembly 24 and the gate 20 via signal connections and is used for evaluating sensor signals from the sensor assembly 24 and driving at least the gate 20 in dependence on the result of evaluation of the sensor signals.

The sensor assembly 24 in connection with the control and evaluation device 30 is used for detecting properties of the bank notes 12 and forming sensor signals representing said properties. The sensor assembly 24 comprises for this purpose at least one sensor; in this exemplary embodiment three sensors are provided, namely, a first sensor 32, in the example an optical sensor which detects optical radiation reflected by the bank note, a second sensor 34, in the example likewise an optical sensor which detects optical radiation transmitted through the bank note, and a third sensor 36, in the example an acoustic sensor, more precisely, an ultrasonic sensor which detects ultrasonic signals coming from the bank note, in particular transmitted thereby.

While a bank note is being transported past, the sensors 32, 34 and 36 detect, according to their function, scan area properties of scan areas on the bank note that are determined by the position of the sensors relative to the bank note, whereby the corresponding sensor signals are formed. Each of the sensors can have a different spatial resolution, i.e. the size and distribution of the detected scan areas on the bank note can vary in dependence on the particular sensor and the transport speed used. Each of the scan areas has assigned thereto a place which represents the position of the scan areas for the particular sensor relative to each other and/or relative to the bank note.

From the analog or digital sensor signals from the sensors 32, 34, 36, the control and evaluation device 30 determines upon a sensor-signal evaluation at least one scan area property and/or at least one bank-note property which are relevant to the check of the bank notes with respect to their condition. Preferably, a plurality of said properties are determined. The bank-note properties characterize the condition of the bank notes, in this example the condition with respect to fitness for use, i.e. in particular machine processibility by bank-note processing apparatus. The bank-note properties used can be in particular e.g. the presence of soiling, stains, tears, adhesive strips, dog-ears and/or holes, and/or the lack of parts of the bank notes and/or the limpness of the bank notes. Said bank-note properties can be determined in dependence on sensor signals from only one of the sensors or at least two of the sensors.

The control and evaluation device 30 has for this purpose in particular, besides corresponding interfaces for the sensors, a processor 38 and a memory 40 connected to the processor 38 and storing at least one computer program with program code upon whose execution the processor 38 controls the apparatus or evaluates the sensor signals, in particular for determining an overall condition of a checked bank note, and drives the transport device 18 according to the evaluation.

In particular, the control and evaluation device 30, more precisely, the processor 38 therein, can, after determination of the bank-note properties, check a criterion for the overall condition of the bank note which includes at least one of the bank-note properties or which depends on at least one bank-note property. The criterion can in particular further include reference data for specifying a permissible condition of the bank note which are preset and stored in the memory 40. The overall condition can for example be given by two categories, 'still fit for circulation' or "fit for use" and "to be destroyed". In dependence on the determined condition, the control and evaluation device 30, in particular the processor 38 therein, drives the transport device 18, more precisely, the gate 20, such that the bank note is transported according to its determined overall condition into the output pocket 26 for deposit or to the shredder 28 for destruction.

For processing bank notes 12, bank notes 12 inserted into the input pocket 14 singly or as a stack are singled by the singler 16 and supplied in singled fashion to the transport device 18 which supplies the singled bank notes 12 to the sensor assembly 24. The latter detects at least one property of the bank notes 12, whereby sensor signals representing the property of the bank note are formed. The control and evaluation device 30 detects the sensor signals, determines in dependence thereon a condition of the particular bank note and drives the gate 20 in dependence on the result such that for example bank notes that are still usable are supplied to the output pocket 26 and bank notes to be destroyed to the shredder 28 for destruction.

In an example, different bank-note properties can be determined as follows.

Soiling of bank notes is characterized by the decrease in optical reflectance, primarily in unprinted areas of the bank notes. A measure of the soiling of the bank notes can thus be determined by the control and evaluation device 30 for example from the sensor signals from the sensor 32. For this purpose, the control and evaluation device 30 can form an average of the reflectance values and/or the variance of the reflectance values and use it for checking the criterion.

Stains on the bank notes can be characterized by their surface area and/or the color contrast with the background. The surface area can be determined by the control and evaluation device 30 for example by counting the above-described scan areas detected by means of the sensor 32 that are covered by stains, then more precisely pixels.

Tears in the bank notes can be recognized by means of the sensor 34 which detects optical radiation transmitted through the bank notes. For characterizing the condition of the bank notes, the control and evaluation device 30 can determine for example the number of tears or the total length of the tears from the data of the sensor 34, in particular by counting the pixels.

Holes in the bank notes can likewise be recognized by means of the sensor 34. For characterizing the condition of the bank notes, the control and evaluation device 30 can determine for example the number of holes or the total surface area of the holes from the signals of the sensor 34, in particular by counting corresponding pixels.

Dog-ears in the bank notes can likewise be recognized by means of the sensor 34. For characterizing the condition of the bank notes, the control and evaluation device 30 can determine for example the number of dog-ears or the total surface area of the dog-ears from the sensor signals of the sensor 34, in particular by counting corresponding pixels.

Adhesive strips on the bank notes 12 can be recognized by means of the sensor 32 which detects optical radiation reflected by the bank notes. For characterizing the condition of the bank notes, the control and evaluation device 30 can for this purpose determine for example the number of adhesive strips or the total length or total surface area of the adhesive strips from the sensor signals of the sensor 32, in particular by counting the pixels.

Missing parts, e.g. security thread, hologram, etc., can likewise be recognized by one or more of the sensors 32, 34 and 36. For characterizing the condition of the bank notes, the control and evaluation device 30 can determine for example the number of missing parts or the total surface area of missing parts from the sensor signals of the sensor or sensors 32, 34 and 36.

The condition with regard to limpness is determined by means of the sensor 36, as described more precisely hereinafter.

For determining the overall condition of the bank notes, the control and evaluation device 30 uses the above-mentioned criterion which can include at least one of the properties. For this purpose, the individual different properties are each assigned a certain value characterizing the condition with regard to said property. For example, a certain soiling is assigned a certain value. However, the same certain value can also be assigned to one or all other properties, so that e.g. a certain number of stains, a certain limpness, a certain number of tears, adhesive strips, dog-ears, holes, missing parts of the bank note, etc., is also assigned the certain value. The individual values can be linked in an exemplary criterion, for example by means of a linear combination. For determining the overall condition of the bank notes, the control and evaluation device 30 then compares the linear combination of the properties characterizing the condition of the bank notes with a preset value and decides for example whether the condition of the bank notes is good or bad, i.e. whether or not they are fit for circulation. This permits a bank note that already has considerable soiling but not enough, taken alone, to result in the condition of the bank note being determined as bad, to be determined as bad if the bank note additionally has e.g. only a few stains and/or tears, etc.

Obviously, a weighting can be carried out in the linear combination of the properties and/or the assignment of the values characterizing the condition of the bank notes to the individual properties. Certain properties, e.g. tears or holes in the bank notes, may be weighted higher than other, less disturbing properties, e.g. dog-ears or stains. It is likewise obvious that other mathematical combinations can be used for evaluating the properties, instead of a linear combination.

In this first exemplary embodiment, however, only the condition value with respect to limpness is used for determining the overall condition.

The sensor 36 for determining limpness is constructed in the example as follows (cf. FIGS. 2 and 3).

The sensor 36 has a plurality of ultrasonic transducers 42 for emitting ultrasound pulses onto the bank note which are disposed both transversely to a transport direction T of the bank notes 12 and longitudinally thereto substantially in a plane parallel to the transport path 22 of the transported bank note 12, and are driven by the control and evaluation device 30. The ultrasonic transducers 42 thus serve as ultrasound transmitters.

Opposite the ultrasonic transducers or transmitters 42 with respect to the transport path 22 there are disposed the same number of ultrasonic transducers 44 serving as ultrasound receivers, which are connected to the control and evaluation device 30 via interfaces not shown in the Figures and schematically shown signal connections such that they can receive ultrasonic waves emanating from a bank note 12 transported along the transport path 22 and caused by irradiation with ultrasound pulses of the ultrasound transmitters 42.

Each of the ultrasound transmitters 42 is assigned one of the ultrasound receivers 44 so as to yield therebetween an ultrasound path 46 extending at least approximately orthogonally to a bank note 12 transported along the transport path 22, along which ultrasound path an ultrasound pulse emitted by the particular ultrasound transmitter 42 runs to the ultrasound receiver 44 assigned thereto. With each pair of ultrasound transmitters and ultrasound receivers assigned thereto or with each ultrasound path 46 in connection with the control and evaluation device 30, a value for the ultrasound transmission of the bank note 12 at the irradiated place can thus be determined.

The ultrasonic transducers 42 or 44 are configured to be well suited for emitting or receiving ultrasound pulses with a duration in the range of about 30 µs in the example and an ultrasound frequency, i.e. a peak frequency of the spectrum of the ultrasound pulse, of about 400 kHz in the example. Further, they are so dimensioned that a spot 48 irradiated upon irradiation with the ultrasound pulses, i.e. a scan area, on a bank note 12 transported along the transport path 22 has in each case a diameter of about 2 mm. Each of the scan areas is assigned the center of the scan area as the place.

The ultrasound transmitters and receivers 42, 44 are so disposed in planes parallel to the bank note 12 in the transport path 22 that values for the ultrasound transmission are detectable for strip-shaped detection areas 50 extending parallel to the transport direction T, as shown in FIG. 4 for an instantaneous view during detection.

Figure 5:
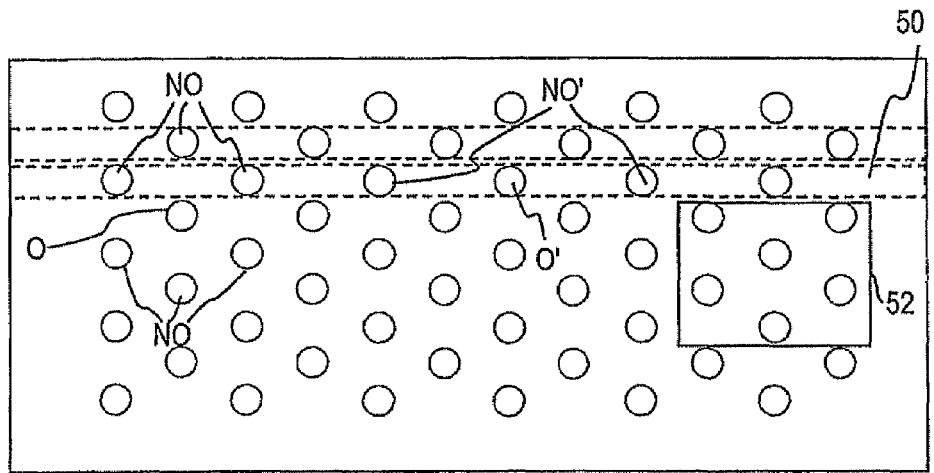

All in all, there can thus result a distribution of scan areas 48 or places, as shown schematically for a bank note 12 in FIG. 4 and in particular FIG. 5, for which transmission values are detectable when the bank note 12 is transported through the ultrasound paths 46 at constant, suitably preset speed and transmission values are detected at preset time intervals during transport. In this exemplary embodiment, the drive is effected independently of the entry of a bank note 12 into the detection area of the sensor 36. To suppress an undesirable reception of ultrasound pulse echoes, the particular ultrasound receiver for an ultrasound path can be switched on with a delay relative to the time of emission of the ultrasound pulse by the ultrasound transmitter for the ultrasound path by somewhat less than the pulse transit time for the ultrasound path, and be switched off again before the double pulse transit time since emission.

There thus results a regular arrangement of the scan areas or places on the bank note 12, in the example a substantially hexagonal arrangement. The arrangement of the ultrasound transmitters and receivers 42, 44 is so selected that the distance of successive places in one of the strips or detection areas 50 is smaller than 1 cm. In the example the distance of nearest neighboring places is thus about 1 cm.

The sensor 36 has in the exemplary embodiment in particular twenty-four ultrasound transmitter/receiver pairs or ultrasound paths 46 which are so disposed that the detection areas 50 or tracks have a distance between 3 and 4 mm.

For detecting the transmission values, the control and evaluation device 30 detects at constant time intervals the sensor signals from the ultrasound receivers 44 which represent the intensity or power of individually received ultrasound pulses as a function of time and thus, due to the constant transport speed, also of place. With reference to said signals the control and evaluation device 30 also determines the entry of a value document into the detection area of the sensor 36. The transmission values are given simply by the received ultrasound pulse energies, assuming a strictly constant transmit power of the ultrasound transmitters 42. In other exemplary embodiments, however, it is also possible to divide the received ultrasound pulse energies by a preset or measured ultrasound pulse energy of transmitted pulses and thus to obtain normalized transmission values.

The determined transmission values are stored as assigned to the places for which they were detected. This can be effected for example in such a way that the transmission values are stored in the memory 40 in the time sequence of their detection separately for each of the detection areas 50. The detection area 50 then corresponds to a coordinate in a direction transverse to the transport direction, and the position in the row along the detection area 50 to a coordinate in the transport direction T.

The frequency at which the ultrasound pulses are successively emitted and the transport speed of the bank note are selected such that at least five transmission values are detected along the transport direction of the bank note in each detection area 50. In the example, transmission values are detected at a distance of 3 mm, preferably 2 mm, along the transport direction or 50 or more transmission values [sic].

Figure 6:
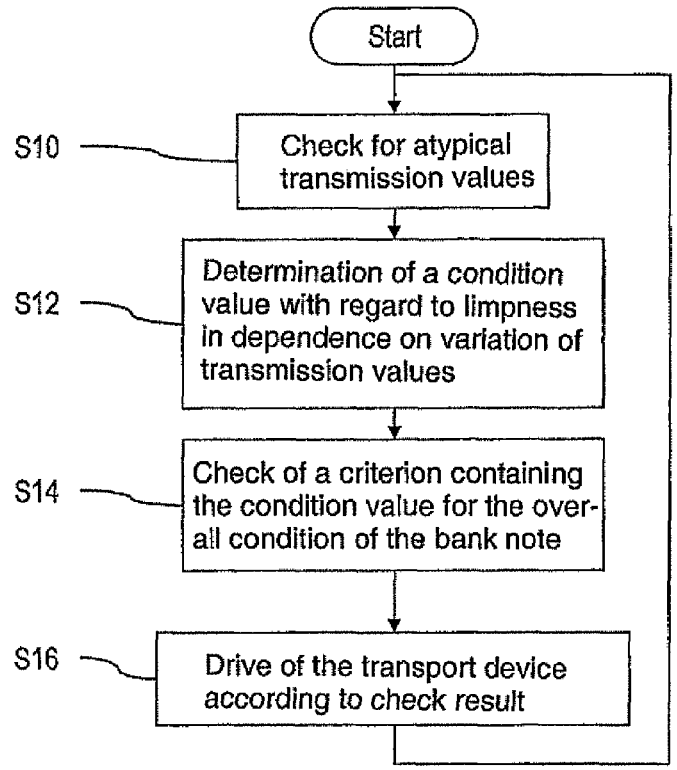
Figure 7:
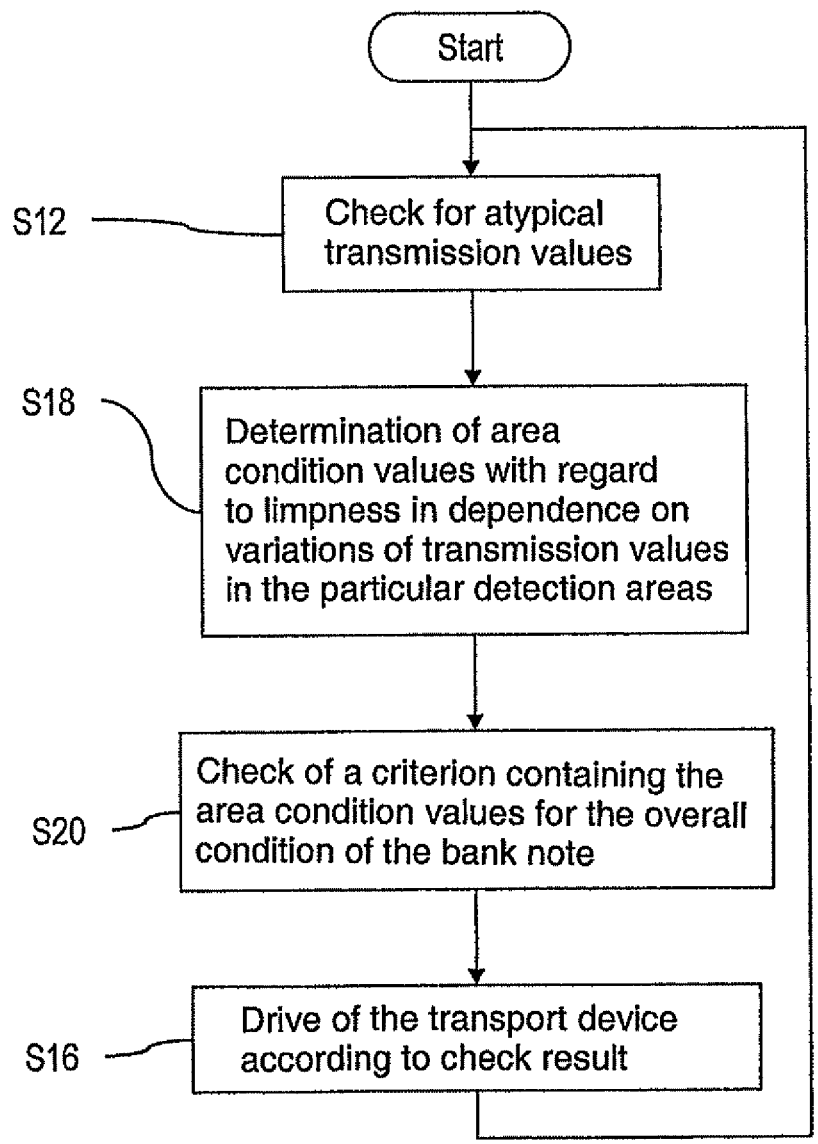

Starting out from said transmission values present for a bank note as a function of place, the control and evaluation device 30, more precisely, the processor 38, now carries out the following method for determining the condition of the bank note upon processing program code of the computer program stored in the memory 40. The method is illustrated very schematically in FIG. 6 as a flow chart.

In step S10, which is in principle optional but is carried out as a preferred variant in this exemplary embodiment, the transmission values are checked as to whether they are deemed atypical according to a preset outlier criterion. Such values can be caused for example by holes or tears in the bank note which lead to very high transmission values.

In this exemplary embodiment, it is checked as the outlier criterion whether one of the transmission values is within a preset range of values. In particular, an average over all transmission values is formed for this purpose and it is checked whether the deviation of the particular transmission value from the average, here their distance from each other, given for example by the absolute difference of transmission value and average, is smaller than a preset threshold value. The threshold value can be expressed for example in decibels and assume the value of about 2 dB when the transmission values are so normalized that the transmission value 1 is determined for an unattenuated ultrasound pulse.

In the following step S12, the control and evaluation device 30, more precisely, the processor 38 therein, determines from the detected transmission values which represent the ultrasound transmission at different places on the bank note and were not recognized as outliers, a condition value which depends on a variation of the transmission values and characterizes the condition of the bank note with regard to limpness. In this exemplary embodiment, the condition value determined is the variance of the transmission values over all places.

The steps S10 and S12 are performed successively here, but can also be nested with each other when a higher processing speed is desired.

In step S14 the control and evaluation device determines a condition of the bank note, which is also designated the overall condition here, for the determined condition value using a preset criterion. In this exemplary embodiment, the criterion checked is the threshold criterion of whether the condition value for limpness, i.e. here the variance, exceeds a preset maximum threshold value determined by experiment. It is of course also possible to use equivalent formulations of the condition.

If the threshold criterion is met, i.e. the threshold value is exceeded by the condition value here, the bank note is classified as "to be destroyed" and the control and evaluation device 30 drives the transport device 18, more precisely, the gate 20, such that the bank note is supplied to the shredder 28 where it is destroyed.

Otherwise the bank note is recognized as "fit for use" and the control and evaluation device 30 drives the transport device 18, more precisely, the gate 20, in step S16 such that the bank note is output to the output pocket 26. It can now be returned to circulation.

The program then jumps back to step S10 to assess the next bank note.

A second preferred embodiment differs from the first exemplary embodiment only by the program code in the memory 40 and thus the method. All other features are unchanged and the explanations on the first exemplary embodiment apply here accordingly.

The computer program now contains program code upon whose execution the processor 38 executes, instead of the steps S12 and S14 in the first exemplary embodiment, the steps S18 and S20 described hereinafter.

In this exemplary embodiment, the condition value is not determined jointly for all transmission values that do not meet the outlier criterion, but rather area condition values are determined separately for each of the detection areas 50 or each of the strips. For a first detection area 50 an area condition value is thus determined, and for different further places on the bank note in a second detection area, for example the directly neighboring detection area or strip, a further area condition value which depends on a variation of the further transmission values for the further places. The same is done for the other detection areas. This determination of the area condition values is effected in step S18.

On the basis of the area condition values, which are likewise determined as variance in this exemplary embodiment, the check of the criterion for the condition of the bank note is now carried out in step S20.

For this purpose, it is checked in this exemplary embodiment whether the average of the area condition values, which can be understood as the condition value with regard to limpness, meets the threshold criterion of the first exemplary embodiment, optionally with another threshold value.

Therefore, the same check is substantially carried out in step S20 as in the first exemplary embodiment in step S14, but with the average of the area condition values being used as the condition value.

In the above-described exemplary embodiments, the condition value or area condition values were determined by calculating the variance, which is a measure of the deviation of the transmission values from the average and thus does not directly consider the surface distribution of the places.

Third and fourth preferred embodiments differ from the first and second exemplary embodiments in that deviations of transmission values for different places from each other, i.e. deviations between transmission values for different places, are used in step S12 and step S18 for considering the variation of the transmission values. For this purpose, the computer program has in the memory 40 only corresponding program code upon whose execution the processor 38 processes the following steps. All other features are unchanged and the explanations on the exemplary embodiments apply here accordingly.

More precisely, these steps use as deviations between transmission values for different places only deviations between transmission values for places whose distance is no greater than a preset maximum distance. In these exemplary embodiments, the maximum distance is the distance of nearest neighboring places, for the third exemplary embodiment the nearest neighbors for a place O therefore being the places NO of the smallest hexagon surrounding the contemplated place O, and for the fourth exemplary embodiment the nearest neighboring places NO' in FIG. 5 on the right and left of a place O'.

Further, the deviation used is the absolute difference. If N designates the number of nearest neighbors for a detection area for the place x, the places $x_i$, i=1, ... N the detection areas or places of the nearest neighboring places and T(y) the transmission value at any place y, then the condition value or area condition value results as $$\frac{1}{M} \sum_X \sum_{i=1}^{N} |T(x_i) - T(x)|,$$

where x runs over the set M of the places used for determining the condition value or area condition value. For the third exemplary embodiment these are the places on the bank note, for the fourth exemplary embodiment the places in a detection area 50. If there occur in the sum places for which no transmission value usable according to the outlier criterion is present, then the corresponding summand is omitted and the number M lowered by 1.

Further preferred embodiments differ from the above-described exemplary embodiments only by the computer program which now contains program code upon whose execution the processor 38 replaces the step S14 by the step described hereinafter. All other features are unchanged and the explanations on the exemplary embodiments apply here accordingly.

The criterion for determining the overall condition of a bank note now not only includes the condition value with regard to limpness, but rather further properties of the bank note which were determined by means of the sensors 32, 34 and 36 as described above, for example the presence of holes, tears, adhesive strips and stains, are also determined and considered in the criterion. For example, a corresponding condition value can be determined for each of said properties, and it is checked as the criterion whether the average over the condition values for the other properties and the overall condition value is smaller than a preset threshold value determined by experiment. If the criterion is met, the condition of the bank notes is "to be destroyed", otherwise the condition is "fit for use".

In the above-described exemplary embodiments it was assumed that the transmission values are detected for places on the bank note that cover it substantially uniformly and, except for a possible edge area, completely. However, bank notes can have areas where the transmission for ultrasound is systematically changed compared to other areas. This applies for example to the watermark 52 which is symbolized in FIG. 5 by a rectangle.

Further preferred embodiments then differ from the above-described exemplary embodiments solely in that transmission values for places in a preset area of the bank note, in the example in the area of the watermark 52, are not used, or used with lower weighting than ones for places outside the area, i.e. watermark, upon determination of the condition value. For this purpose, the apparatus has a device for determining a type, for example the denomination, of a supplied bank note, and the memory stores data representing the position of the watermark on a bank note of the particular type. Furthermore, a device is provided that determines the orientation of the bank notes in the transport device 18. This can be constituted for example by the sensor 32 and corresponding program code in the computer program. Further, the computer program is modified to the effect that the contributions to the sums are weighted upon determination of the condition values or area condition values, whereby they are weighted only low for summands in which the transmission occurs for a place in the area of the watermark or are completely omitted in other exemplary embodiments. All other steps are unchanged. Said places are determined with reference to the type of bank note, the stored position data for the watermark 52 and the orientation of the bank note.

In another preferred embodiment, transmission values for places in a preset area, in the example outside the watermark 52, can be weighted higher than transmission values for places in the area of the watermark 52 upon determination of the condition value.

A further preferred embodiment differs from the previous exemplary embodiments in that a systematic change of transmission is not determined by a change of the weighting of the corresponding contributions to the condition value or area condition value, but rather a "correction" is performed in such a way that the corrected transmission values, in good approximation, only vary statistically due to limpness. For this purpose, departing from the exemplary embodiments with special consideration of the watermark, the position data thereof are not stored, but rather a preset transmission profile of the bank note, which serves as a reference and has, as a function of place, transmission values for example averaged over a large number of freshly printed or unused bank notes of a preset type. The representation of the preset transmission profile can be effected by a table or by a parametric representation. All other features are unchanged and the explanations on the last two exemplary embodiments apply here accordingly.

The computer program now contains program code upon whose execution the processor, depending on the execution, subtracts values corresponding to the transmission profile for correction from the determined transmission values before or upon determination of the condition value or area condition values.

All following steps remain unchanged.

In further exemplary embodiments, a spectrum of the transmission values can be used in the condition values or area condition values for considering the variation. In particular, a power spectrum of the transmission values can be determined, for which purpose in particular known fast Fourier transform (FFT) algorithms can be used.

In further alternative embodiments, a distribution function of the transmission values can be determined and used for considering the variation. After determination of the distribution function, i.e. the number of transmission values in preset bins, it is possible to determine for example the half width of the distribution function and use it as the condition value or area condition value.

Another preferred embodiment differs from the first exemplary embodiment in that the ultrasonic transducers are configured to be well suited for emitting or receiving ultrasound pulses with a duration in the range of about 45 μs and an ultrasound frequency, i.e. a peak frequency of the spectrum of the ultrasound pulse, of about 300 kHz. Further, they are so dimensioned that a spot irradiated upon irradiation with the ultrasound pulses on a bank note transported along the transport path 22 has a diameter of about 3 mm.

In other embodiments, the ultrasound paths can also be inclined relative to the plane of the bank note under examination to avoid the influence of echoes upon use of ultrasound pulses.

Further, the ultrasound can also be emitted continuously instead of in pulses. In this case, the ultrasound paths are preferably likewise inclined relative to the bank note under examination to avoid the occurrence of stationary waves.

The invention claimed is:

1. A method for assessing a condition of at least one value document with regard to limpness using an ultrasound device to obtain transmission values, comprising the steps of:
    determining from transmission values representing the ultrasound transmission at different places on the value document a condition value, the condition value depending on a local variation of the transmission values and characterizing the condition of the value document with regard to limpness, wherein the local variation of the transmission values is a change or fluctuation between the transmission values at different places and not an average of transmission values; and
    determining a condition of the value document from the condition value using a preset criterion.

2. The method according to claim 1, wherein ultrasound pulses are emitted onto at least two of the different places on the value document, and ultrasound pulses emanating from the places as a result of the ultrasound pulses are detected so as to form the transmission values.

3. The method according to claim 1, wherein the ultrasound has an ultrasound frequency greater than 300 kHz.

4. The method according to claim 1, wherein spots on the value document irradiated in each case by the ultrasound have a diameter smaller than 3.5 mm.

5. The method according to claim 1, wherein the places are distributed regularly.

6. The method according to claim 1, wherein the places are disposed within a linear strip parallel to a transport direction of the value document.

7. The method according to claim 1, wherein the places are disposed within at least two strips.

8. The method according to claim 1, wherein there is determined from further transmission values for different further places on the value document a further condition value depending on a variation of the further transmission values for the further places, and the preset criterion additionally includes the further condition value.

9. The method according to claim 1, wherein transmission values for the places in a preset area of the value document are not used, or used with lower weighting than ones for places outside the area, upon determination of the condition value.

10. The method according to claim 1, wherein transmission values for the places, in a preset area are weighted higher than transmission values for other places upon determination of the condition value.

11. The method according to claim 1, wherein the transmission values are corrected with respect to a transmission profile preset for the value document, before or upon determination of the condition value.

12. The method according to claim 1, wherein deviations of the transmission values from a preset value are used for considering the variation.

13. The method according to claim 1, wherein deviations between the transmission values at different places are used for considering the variation.

14. The method according to claim 13, wherein the deviations between the transmission values at different places used are only deviations between transmission values for places whose distance is no greater than a preset maximum distance.

15. The method according to claim 1, wherein a spectrum of the transmission values is used for considering the variation.

16. The method according to claim 1, wherein transmission values deemed atypical according to a preset outlier criterion are not considered, or considered less strongly than other transmission values, upon determination of the condition value.

17. The method according to claim 1, further comprising the step of checking as an outlier criterion whether one of the transmission values is within a preset range.

18. An evaluation device for assessing a condition of at least one value document with regard to limpness, wherein the device is configured to:
determine from transmission values representing the ultrasound transmission at different places on the value document a condition value, the condition value depending on a local variation of the transmission values and characterizing the condition of the value document with regard to limpness, wherein the local variation is a change or fluctuation between the transmission values at different places and not an average of transmission values; and
determine a condition of the value document from the condition value using a preset criterion.

19. The evaluation device according to claim 18, comprising a processor, a memory storing a computer program for execution by the processor, and an interface for detecting signals or data from which the transmission values and/or the variation of the transmission values can be determined or which represent the transmission values.

20. The evaluation device according to claim 18, wherein the device is configured for determining from further transmission values for different further places on the value document a further condition value which depends on a variation of the further transmission values for the further places, and wherein the preset criterion additionally includes the further condition value.

21. The evaluation device according to claim 18, wherein the device is configured such that transmission values for places in a preset area of the value document are not used, or used with lower weighting than ones for places outside the area, upon determination of the condition value.

22. The evaluation device according to claim 18, wherein the device is configured such that transmission values for places in a preset area are weighted higher than transmission values for other places upon determination of the condition value.

23. The evaluation device according to claim 18, wherein the device is configured such that the transmission values are corrected with respect to a transmission profile preset for the value document, before or upon determination of the condition value.

24. The evaluation device according to claim 18, wherein the device is configured for using deviations of the transmission values from a preset value, including an average of the transmission values, for considering the variation.

25. The evaluation device according to claim 18, wherein the device is configured for using deviations between the transmission values at different places for considering the variation.

26. The evaluation device according to claim 18, wherein the device is configured for using as deviations between the transmission values at different places only deviations between transmission values for places whose distance is no greater than a preset maximum distance.

27. The evaluation device according to claim 18, wherein the device is configured for using a spectrum of the transmission values for considering the variation.

28. The evaluation device according to claim 18, wherein the device is configured for not considering transmission values deemed atypical according to a preset outlier criterion, or considering them less strongly than other transmission values, upon determination of the condition value.

29. The evaluation device according to claim 28, wherein the device is configured so as to check as an outlier criterion whether one of the transmission values is within a preset range.

30. An apparatus for assessing a condition of at least one sheet-shaped value document with regard to limpness, comprising
at least one ultrasound transmitter and one ultrasound receiver located opposite each other to form an ultrasound path for a detection of the transmission at a place on the value document,
an evaluation device according to claim 18, and
an interface between the ultrasound receiver and the evaluation device by means of which transmission signals from the ultrasound receiver which represent transmission values are supplied to the evaluation device for assessing the condition of the value document.

31. The apparatus according to claim 30, wherein the evaluation device is connected to the ultrasound transmitter for the drive thereof and configured for driving the ultrasound transmitter to emit ultrasound pulses.

32. The apparatus according to claim 30, wherein the ultrasound transmitter is configured for emitting ultrasound at an ultrasound frequency greater than 300 kHz.

33. The apparatus according to claim 30, wherein the ultrasound transmitter is configured for emitting ultrasound which irradiates a spot with a diameter smaller than 3.5 mm when impinging upon a value document disposed at a preset distance from the ultrasonic sensor.

34. The apparatus according to claim 30, further comprising a transport device for transporting the value document through the ultrasound path and wherein the evaluation device is configured for successively detecting corresponding transmission values in at least five different places on the value document and evaluating them.

35. The apparatus according to claim 30, further comprising at least one further ultrasound path and wherein the evaluation device is configured for evaluating transmission signals detected along the further ultrasound path.

36. The apparatus according to claim 30, further comprising at least one further ultrasound receiver for detecting transmission values which is spaced from the at least one ultrasound receiver in a preset direction.

37. The apparatus according to claim 30, wherein the evaluation device is configured so that the transmission values or further transmission values are determined from transmission signals for the places which are determined by means of the ultrasound path or further ultrasound path.

38. A non-transitory computer-readable data carrier storing a computer program for execution by means of a data processing device having a processor which contains program code upon whose execution the processor carries out the method according to claim 1, the program determines from transmission values representing the ultrasound transmission at different places on the value document a condition value, the condition value depending on a local variation of the transmission values and characterizing the condition of the value document with regard to limpness, wherein the local variation of the transmission values is a change or fluctuation between the transmission values at different places and not an average of transmission values; and determines a condition of the value document from the condition value using a preset criterion.

39. The non-transitory computer-readable data carrier according to claim 38, comprising program code upon whose execution the processor determines from further transmission values for different further places on the value document a further condition value which depends on a variation of the further transmission values for the further places, which contains program code, so that the preset criterion additionally includes the further condition value.

40. The non-transitory computer-readable data carrier according to claim 38, comprising program code upon whose execution the processor does not use transmission values for places in a preset area of the value document, or uses them with lower weighting than ones for places outside the area, upon determination of the condition value.

41. The non-transitory computer-readable data carrier according to claim 38, comprising program code upon whose execution the processor weights transmission values for places in a preset area higher than transmission values for other places upon determination of the condition value.

42. The non-transitory computer-readable data carrier according to claim 38, comprising program code upon whose execution the processor corrects the transmission values with respect to a transmission profile preset for the value document, before or upon determination of the condition value.

43. The non-transitory computer-readable data carrier according to claim 38, comprising program code upon whose execution the processor uses deviations of the transmission values from a preset value, preferably an average of the transmission values, for considering the variation.

44. The non-transitory computer-readable data carrier according to claim 38, comprising program code upon whose execution the processor uses deviations between the transmission values at different places for considering the variation.

45. The non-transitory computer-readable data carrier according to claim 38, comprising program code upon whose execution the processor uses as deviations between the transmission values at different places only deviations between transmission values for places whose distance is no greater than a preset maximum distance.

46. The non-transitory computer-readable data carrier according to claim 38, comprising program code upon whose execution the processor does not consider transmission values deemed atypical according to a preset outlier criterion, or considers them less strongly than other transmission values, upon determination of the condition value.

47. The non-transitory computer-readable data carrier according to claim 46, comprising program code upon whose execution the processor checks as the outlier criterion whether one of the transmission values is within a preset range.

48. The method according to claim 12, wherein the preset value is an average of the transmission values.

\* \* \* \* \*